United States Patent [19]
Holland et al.

[11] Patent Number: 5,454,722
[45] Date of Patent: Oct. 3, 1995

[54] INTERACTIVE MULTIMEDIA EYE SURGERY TRAINING APPARATUS AND METHOD

[75] Inventors: Simon Holland, Vancouver, Canada; Ben Childers, Seattle, Wash.

[73] Assignee: Project Orbis International, Inc., New York, N.Y.

[21] Appl. No.: 151,538

[22] Filed: Nov. 12, 1993

[51] Int. Cl.⁶ .............................. G06F 15/00; G09B 5/00
[52] U.S. Cl. .................. 434/271; 434/308; 434/307 R; 364/413.02
[58] Field of Search .................... 434/262, 270, 434/271, 308, 307 R, 318, 219, 224; 364/413.01, 413.02, 413.13

[56] References Cited

U.S. PATENT DOCUMENTS

| | | | |
|---|---|---|---|
| 4,305,131 | 12/1981 | Best | 364/521 |
| 4,360,345 | 11/1982 | Hon | 434/262 |
| 4,481,412 | 11/1984 | Fields | 235/472 |
| 4,651,201 | 3/1987 | Schoolman | 358/98 |
| 4,749,354 | 6/1988 | Kerman | 434/321 |
| 4,797,104 | 1/1989 | Laerdal et al. | 434/265 |
| 4,804,328 | 2/1989 | Barrabee | 434/308 |
| 4,812,125 | 3/1989 | Strashun | 434/224 |
| 4,839,822 | 6/1989 | Dormond et al. | 364/413.02 |
| 4,850,876 | 7/1989 | Lutaenko et al. | 434/265 |
| 4,855,842 | 8/1989 | Hayes et al. | 358/342 |
| 4,907,973 | 3/1990 | Hon | 434/262 |
| 5,049,147 | 9/1991 | Danon | 606/10 |
| 5,166,875 | 11/1992 | Machida | 364/413.13 |
| 5,179,654 | 1/1993 | Richards et al. | 395/157 |

*Primary Examiner*—John G. Weiss
*Attorney, Agent, or Firm*—Skadden, Arps, Slate, Meagher & Flom

[57] ABSTRACT

The present invention relates to a interactive computer system for use in training persons in surgical procedures in remote locations. The system employs visual, audio and/or textual data bases to provide training to students of such procedures using a personal computer based system with graphics and multimedia capabilities.

11 Claims, 12 Drawing Sheets

INTERACTIVE MULTIMEDIA EYE SURGERY TRAINING APPARATUS AND METHOD

FIELD OF THE INVENTION

The present invention relates to a technique for training persons in surgical procedures using an interactive multimedia computer system.

BACKGROUND OF THE INVENTION

Doctors, such as ophthalmologists, are currently trained with traditional "hands on" methods of observation and apprenticeship. A student of a new ophthalmic procedure is generally dependent on experienced ophthalmologists for an introduction to the basic principles of the new procedure, a demonstration in performing the procedure and supervision during the initial attempts at performing the procedure. These traditional methods of training require constant supervision by highly skilled ophthalmologists, thus, limiting the number of persons who may be competently trained to perform such new procedures in a specified amount of time.

Organizations which have sought to train medical personnel in developing countries have found these traditional methods of training especially frustrating because of the limited availability of skilled persons and necessary facilities to provide such training. For instance, Project ORBIS, based in New York, N.Y., which is dedicated to the reduction of world blindness through education, employs a specially equipped aircraft with highly skilled medical personnel who travel to developing countries around the world to train student doctors in advanced procedures for treating blindness. The students of the new procedures must be trained in all possible variations and consequences relating to the procedures. The students must then be provided with an opportunity to observe sample procedures and to perform the procedure under the supervision of experienced personnel. The number of persons which the organization may train effectively using these training techniques is limited to a few select student doctors. Consequently, the organization has not been able to adequately train a sufficient numbers of doctors to treat such conditions as cataracts, which currently affect an estimated thirty-five million people worldwide.

Although certain systems have been suggested in the prior art for training students in surgical procedures in general, no adequate system has been provided for training students in advanced ophthalmic surgical techniques. For example, U.S. Pat. No. 4,804,328 to Kent P. Barrabee discloses an interactive audio-visual teaching technique and U.S. Pat. No. 4,481,412 to Craig I. Fields teaches an interactive video disc training system with bar code access for use with a workbook. None of the systems described therein provide for a training device which may be used to train surgeons in advanced surgical techniques such that it could be effectively used in a remote location in conjunction with the training programs employed by organizations such as Project Orbis. Among other things, these prior art systems are not sufficiently self contained and non-cumbersome so as to effectively provide live or graphical display in combination with textual and/or audio presentations so as to be effectively used in training student doctors in advanced surgical procedures without constant direct supervision and instruction.

SUMMARY OF THE INVENTION

It is therefore an object of the present invention to provide a means of training persons in remote locations in advanced surgical techniques without constant supervision by training personnel by providing useful detailed instruction in conjunction with visual display for a specified procedure.

It is a further object of this invention to provide training instruction in a self-contained computer based multimedia interactive format which is easily adaptable to different foreign languages, easily transportable, useable in remote locations, inexpensive and adaptable to future modifications so that the system may be easily and economically employed in various developing countries around the world.

It is a further object of the present invention to provide a variation of the foregoing technique which is specifically adapted for training persons in eye surgery techniques.

The present system comprises a self contained interactive multimedia computer system which is preprogrammed to provide audio-visual feedback to a user (i.e., student of surgical procedure) in a selected language for a specified surgical procedure. The system display provides a user with a selection of surgical procedures to choose from with an on line help menu and simple instructions in a selected language. Upon selection of a specified procedure, the system presents the user with a scenario, which may include visual representation of the area to be operated upon, and a general description of the scenario. The system may also provide means for written and/or verbal communication with the user. Once presented with a scenario, the user selects various surgical instruments and steps in performing the procedure from among a plurality of possible selections. Once selected, the computer system displays, via video and/or audio display, the consequences of the selected action and provides the user with feedback regarding the result of the selected action.

The system may also be provided with a display means which includes "live footage" display, text display and additional graphical displays. This display provides a user with visual footage of the selected action, an explanation of the events resulting from the selection, an opportunity to obtain additional information and to review the preceding events, and an opportunity to view graphical representation of the events which have transpired.

The system is designed so that it may be easily converted between different languages requirements by updating predetermined data base materials without reprogramming.

The system may also be provided with a recording mechanism, such as a video cassette recorder (VCR), for recording all outputs and displays presented during the course of any training session. This recording mechanism provides a user with the opportunity to review the training exercise at their own leisure and for subsequent review of a students progress by supervisory personnel.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

By way of example, the present invention is illustrated in terms of a system for use in training medical personnel in the phacoemulsification ("Phaco/IOL") surgical technique for cataract extraction with lens implantation. The example application described herein is only one example application of the present invention and is provided for the purpose of better explaining the present invention. The present invention may be applied to any number of other ophthalmic and general surgical procedures. Thus, the present invention should not be limited to the specific example of Phaco/IOL described herein.

The Hardware

Figure 1:
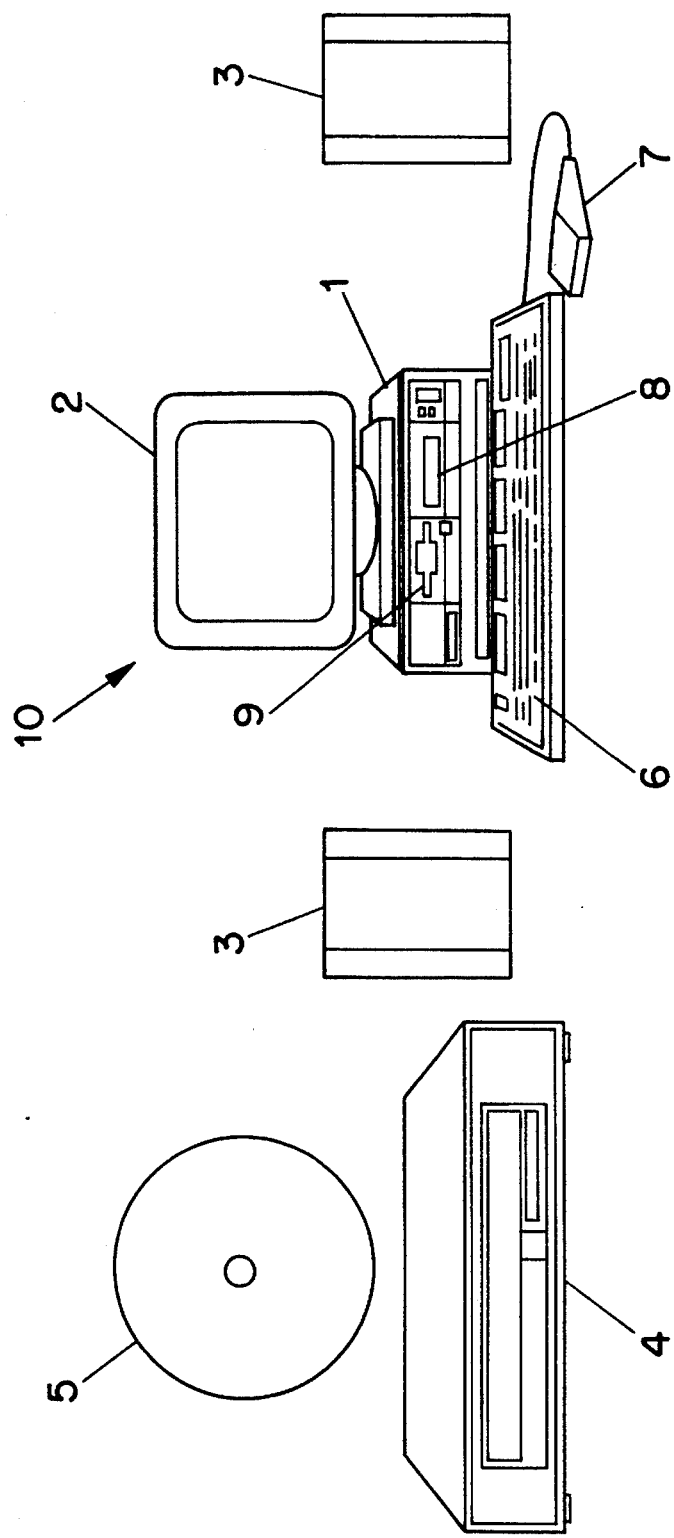
FIG. 1 is a block diagram of a computer system used in a preferred embodiment of the present invention.

Shown in FIG. 1 is an example of a multimedia computer system 10 which could be employed to implement the present invention. In FIG. 1, a computer system 10 is shown having a 486 based 33 Mhz CPU based computer 1 with an internal hard drive, a disk drive 9 (which could also include a CD-ROM reader 8), a monitor 2, speakers 3 and a laser disk player 4 for playing a laser disk 5. The computer system 10 may also include a mouse 7 or a keyboard 6 which permits a user (not shown) to command and interface with the computer system 10. The monitor 2 may incorporate touch screen technology which would permit a user to select among various options by touching a specific area of the screen.

The computer system 10 could also incorporate other user interface devices such as a voice command recognition system, a pointer system or a dedicated command controller, either of which would permit a user to communicate commands and instructions to the computer system 10. The implementation of other user interface devices would be obvious to those skilled in the art and will not be discussed further herein.

In a preferred embodiment of the present invention, the laser disk player 4 is connected to the computer 1 through an internal board such as a Truevision Bravado 16 Bit Multimedia Engine available from the Truevision Corporation of Indianapolis, Ind.

The computer system 10 could also be provided with a separate recording mechanism 100 for recording all, or a selected portion of, the output and displays prescribed during the course of any training session. The recording mechanism 100 may be any standard VCR, or any other device which could record data in either analog or digital form and which could later be replayed and reviewed at the convenience of the user.

In a preferred embodiment, the computer system 10 includes a Truevision Bravado Encoder available from Truevision Corporation of Indianapolis, Ind. which Encoder delivers the video and audio display output of the system over a standard cable to a standard VCR recorder. The Encoder is preferably located within an expansion slot of the computer 1.

The various hardware components of the computer system 10 are coupled to the computer 1, via standard cable lines (not shown) in a manner well known to those skilled in the art. Alternatively, the components may be connected to the computer 1 via commercially available wireless communications networks.

Preferably, the computer system 10 should be portable, and simple to set up and use in remote areas. The computer system 10 should also be capable of receiving upgrades in hardware and software through existing expansion slots and connections. The computer system 10 should also be provided with a modem for receiving new and updated data at remote locations without the need for technical personnel.

The Interactive Programming

In a preferred embodiment of the present invention, the computer system 10 is programmed to provide an interactive surgical training system for the Phaco/IOL surgical procedure.

The computer system 10 is programmed to provide an initial opening screen on the display monitor 2. The initial screen introduces the system to the user and provides the user with a menu from which he or she may select either a "help" program which provides a visual, audio and textual explanation of the various components of the system, or to begin the training exercise.

If the user elects to begin the exercise, a Main Menu screen is provided which permits the user to select between different surgical procedures available on the system. Once the user makes a selection from the Main Menu Screen the user is provided another screen which lists various steps in the selected procedure to which the user may proceed for instruction. A flow chart of the Main Menu possibilities relating to the PHACO/IOL procedure is shown in FIG. 2.

Figure 2:
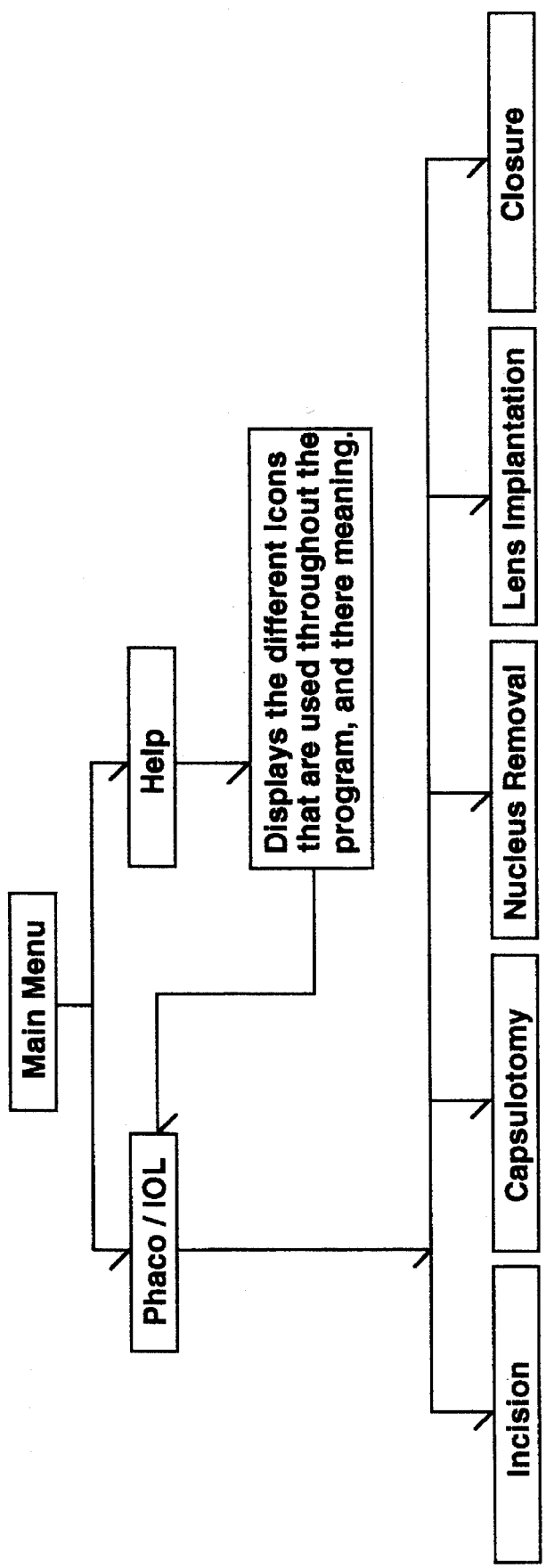
FIGS. 2 and 4–12 are block representations of flow charts for a preferred embodiment of the present invention.

As shown in FIG. 2, once the user proceeds from the Main Menu screen to the PHACO/IOL screen, the user may select either a help menu, which is preferably made available at every screen of the program wherein a user may select various commands, or one of several specific steps in the PHACO/IOL procedure for which detailed instruction is available. For example, the user may elect to receive further instruction on the steps of incision, capsulotomy, nucleus removal, lens implantation, and closure. Once the user selects a specific step in the procedure, the system automatically updates the monitor to display the appropriate output.

Figure 3:
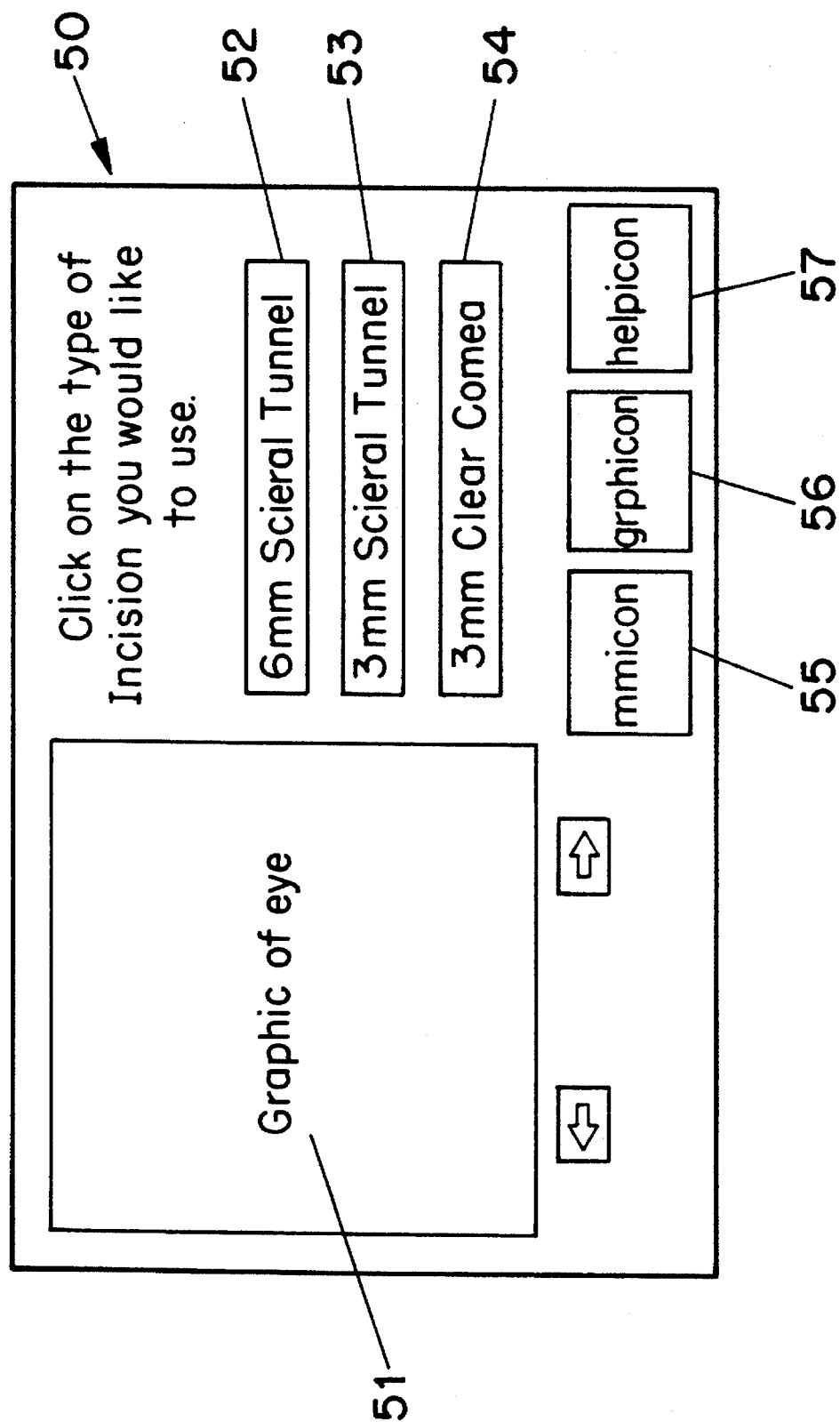
FIG. 3 is a sample representation of a display screen for a preferred embodiment of the present invention.

In the example given, if the user selects the incision step, the display monitor 2 will display a screen 50 such as that represented in FIG. 3. The screen 50 includes a box 51 which displays either a graphical or video picture of the eye prior to the incision step, thereby presenting an initial scenario of a physical area to be operated on. In addition to box 51, the screen 50 includes button boxes 52, 53, and 54 which denote different incision types that could be used to perform the incision step. In FIG. 3, the user is given the choice between three incision types, a 6 mm Scleral Tunnel Incision 52, 3 mm Scleral Tunnel Incision 53, and a 3 mm Clear Cornea Incision 54.

In addition to the video display on the server 50, the user is provided with audio instruction concurring over the available selections. For instance, in the correction video display depicted in FIG. 3, the user might receive an audio message that stated: "You have chosen incision. Please make a selection from the following incision types. 6 mm Scleral Tunnel, 3 mm Scleral Tunnel, or 3 mm Clear Cornea. There are three icons at the bottom of the page which can be clicked on at any point throughout the program. The button on the left will take you back to the Main Menu. The button in the center takes you to a Sub-Menu for more information on that particular section of the program. Finally the help menu. All these icons will be explained in better detail in the Help Menu. Please select an incision type, or choose from any of the other icons." The three icons are represented in FIG. 3 as boxes 55, 56 and 57.

The system will thereafter provide different outputs to the user in accordance with the flow charts provided in FIGS. 4–12 and further described herein depending on the user's initial selections.

Figure 4:
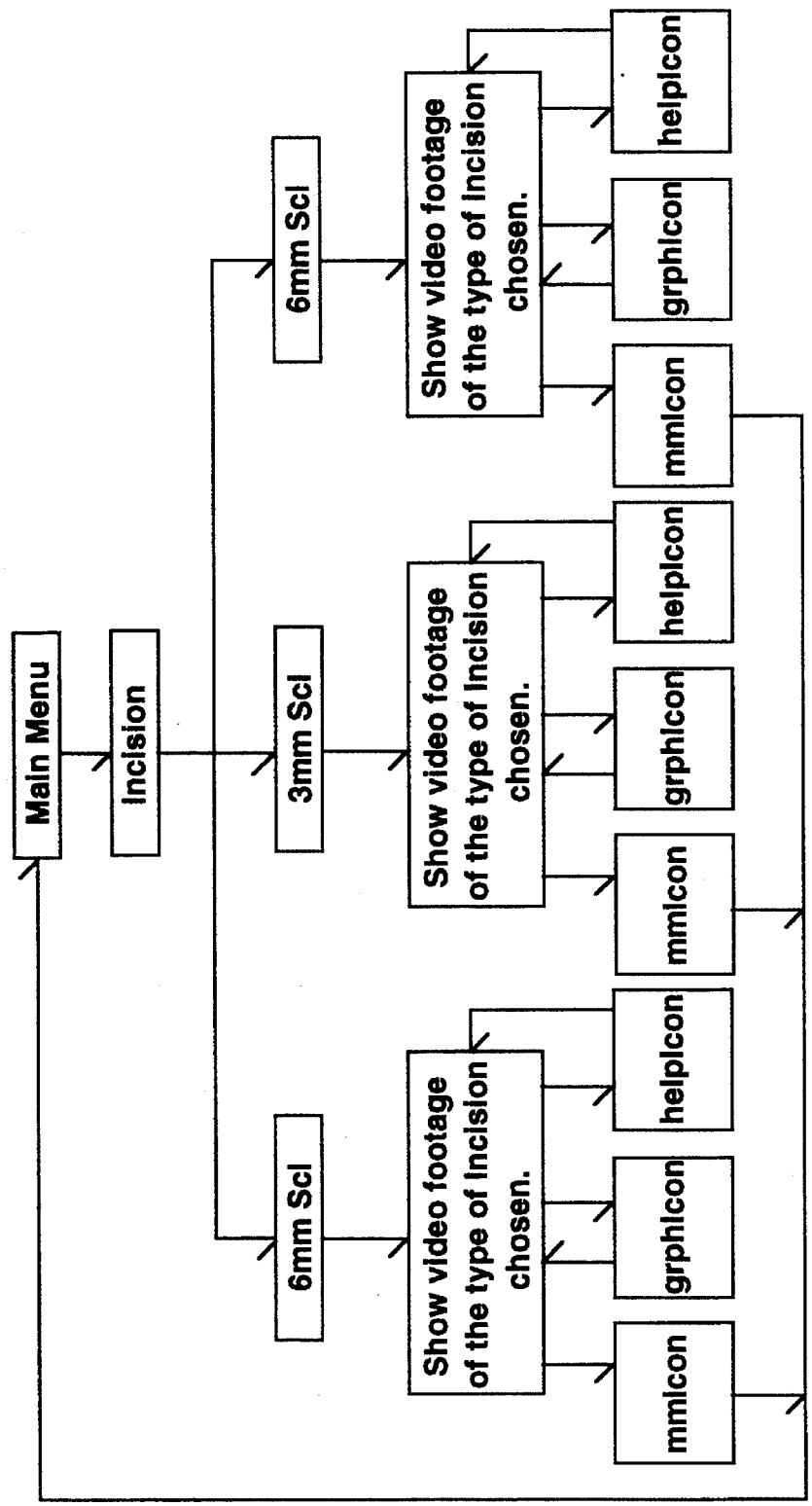

Shown in FIG. 4 is a flow chart for the possible outputs and consequences resulting from the selections available to the user in FIG. 3. As shown in FIG. 4, after one of the incision types is selected, box 51 of the video screen 50 is continuously updated with data to show a live video display of the procedure being performed in accordance with the selected incision type. The screen 50 is also provided with forward, backward, and freeze buttons below box 51 to aid the user in reviewing the procedure being illustrated. The video display is preferably provided.

In addition to the graphics portion, which is preferably a live video display of a previously made incision, recorded and stored on a laser disk 5, the system comprises an audio portion which describes the procedure that is being illustrated in the graphical portion of the display area. A separate display area on the screen may also provide textual explanation of the events occurring in the graphics portion of the display area. By way of illustration, if a user selects a 6 mm Scleral Tunnel incision in the display screen shown in FIG. 3, the computer system would retrieve the appropriate video footage stored on the video disk, update the right portion of the screen to provide a textual explanation of the selected procedure, and provide an audio message which would state: "You have chosen a 6 mm Scleral Tunnel incision. After good hemostasis has been obtained with eraser cautery, a curved 0.3 mm groove is made with the diamond knife between 1 and 1.5 mm back from the limbus. This wound is then shelved and tunneled into clear cornea, along its entire length. A stab wound is made into the anterior chamber for the capsulotomy, and the capsulotomy is then performed. The shelf aspects of the wound allows for healing to occur over a broader surface."

Figure 5:
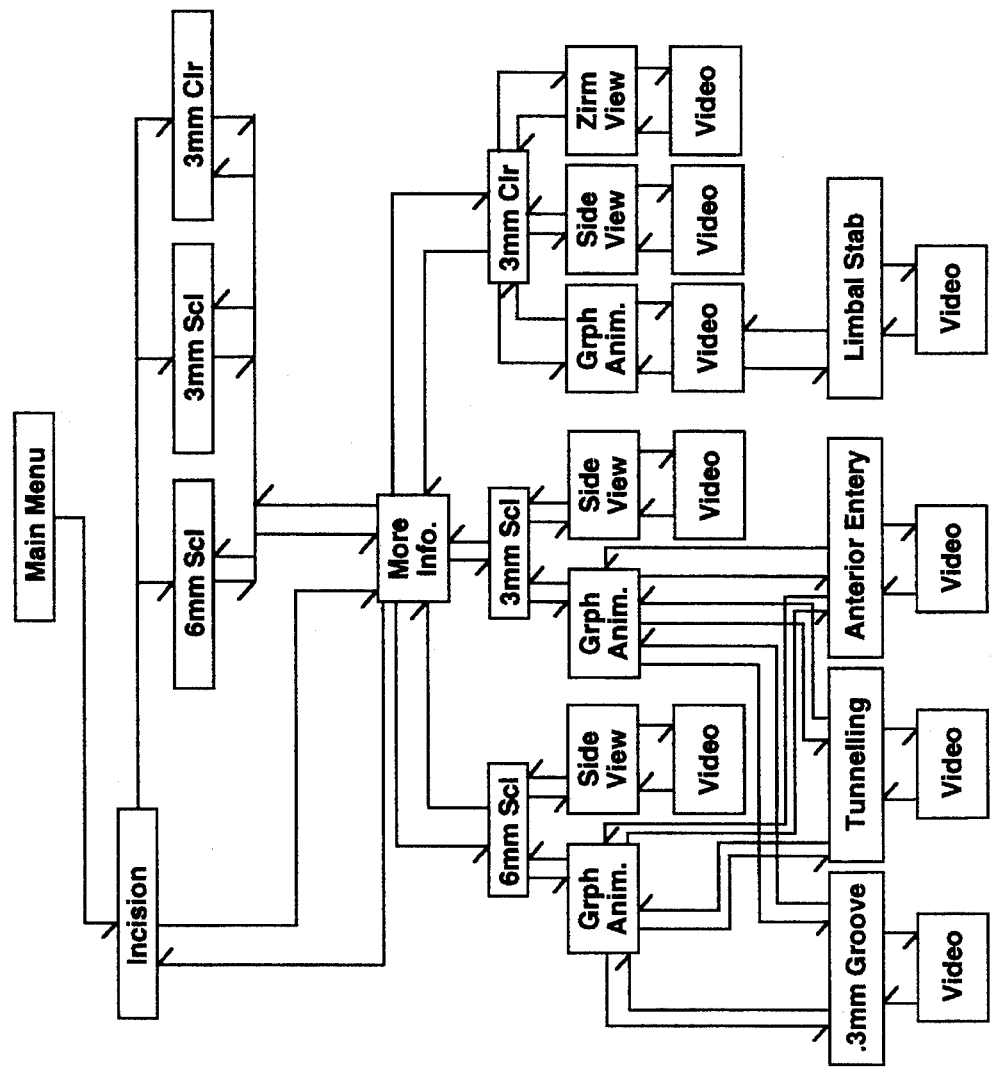
Figure 6:
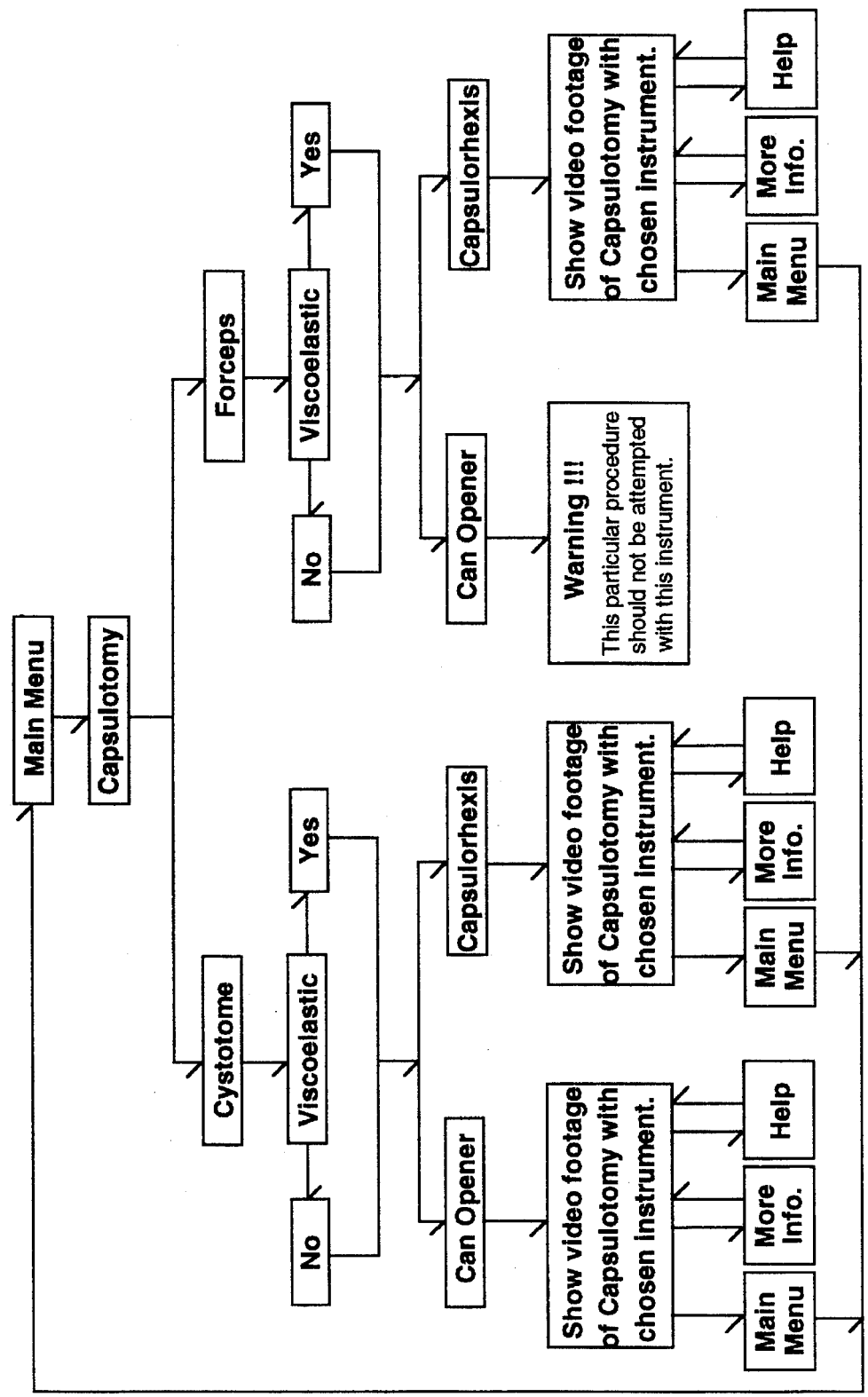
Figure 7:
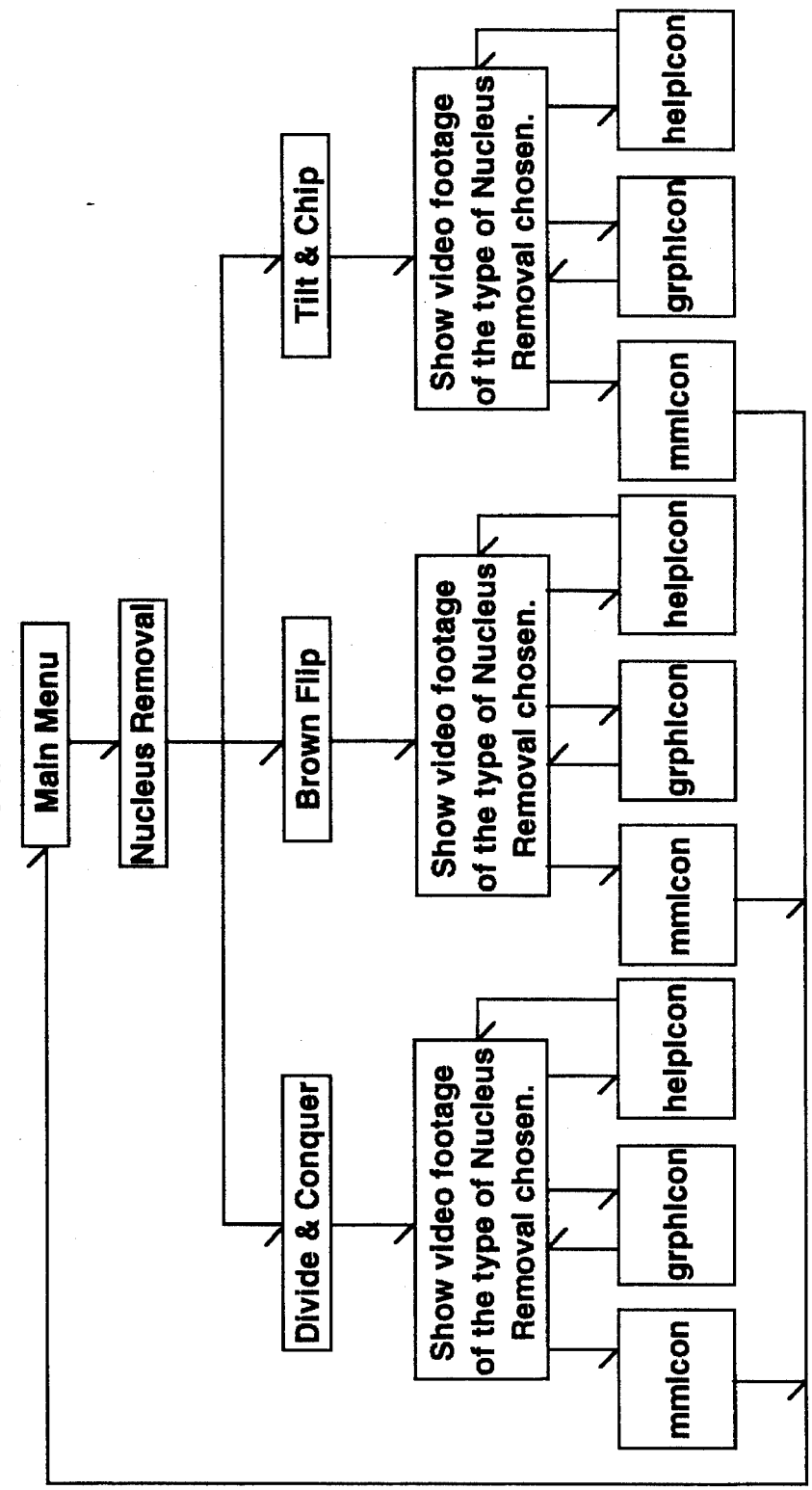
Figure 8:
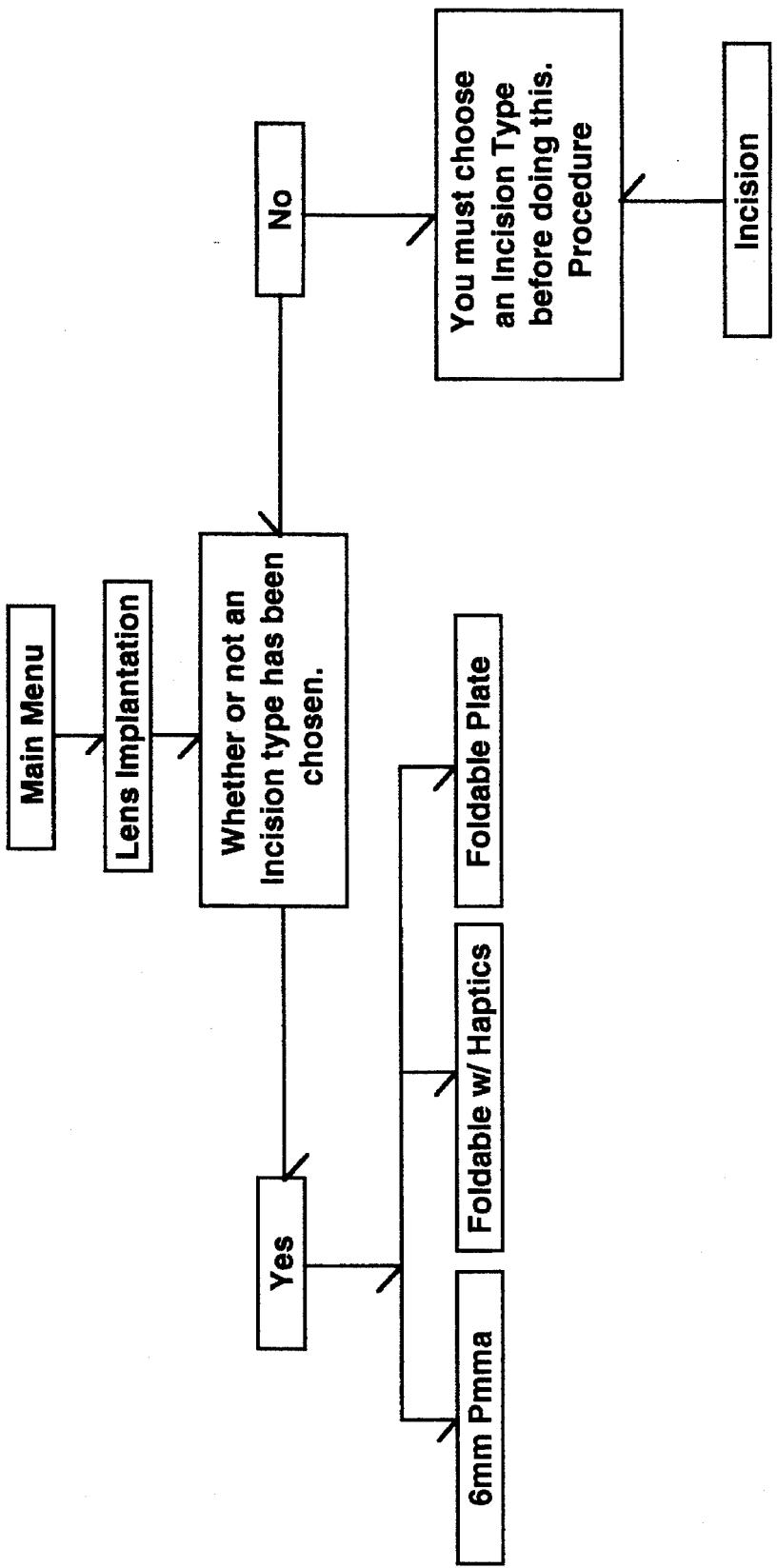
Figure 9:
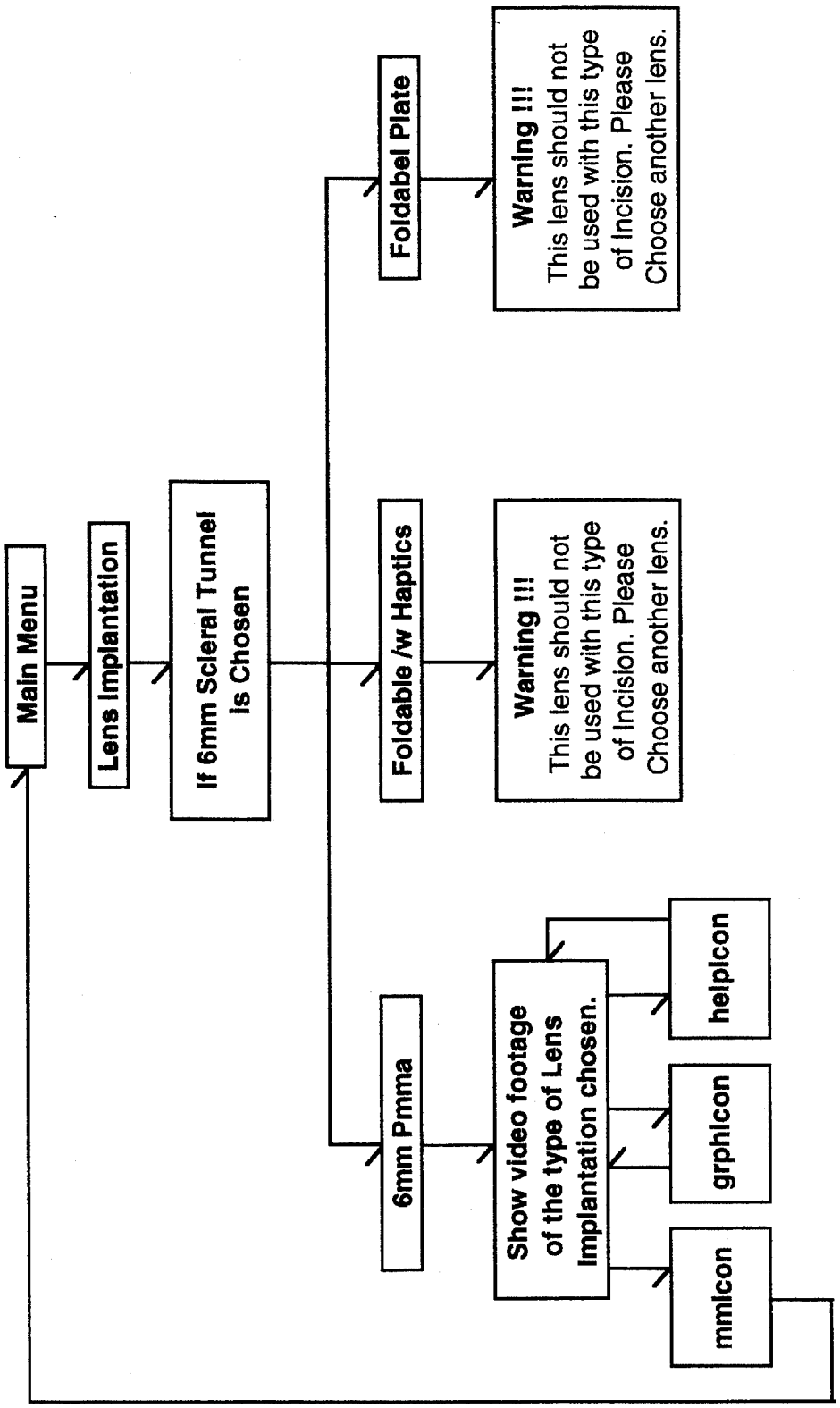
Figure 10:
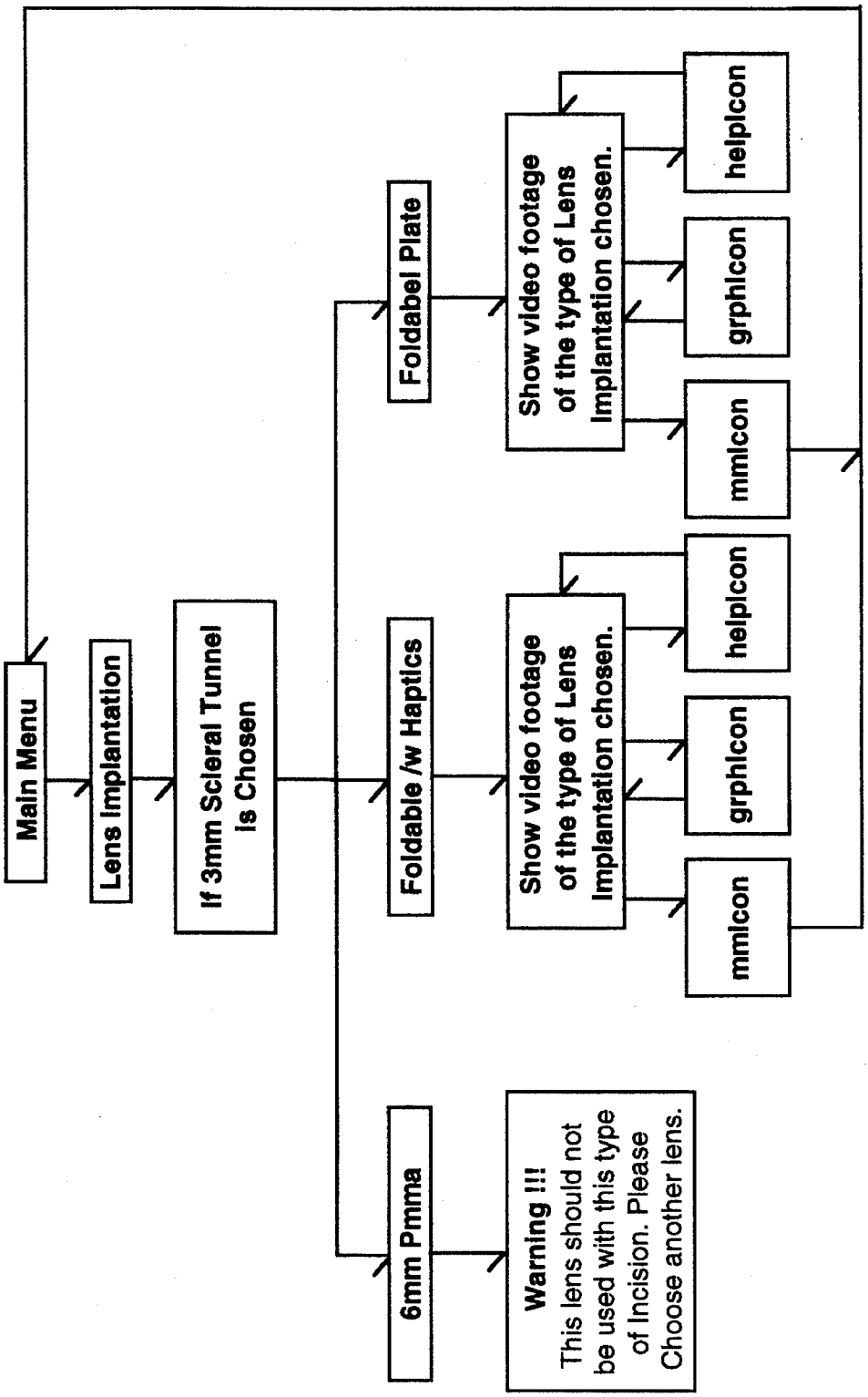
Figure 11:
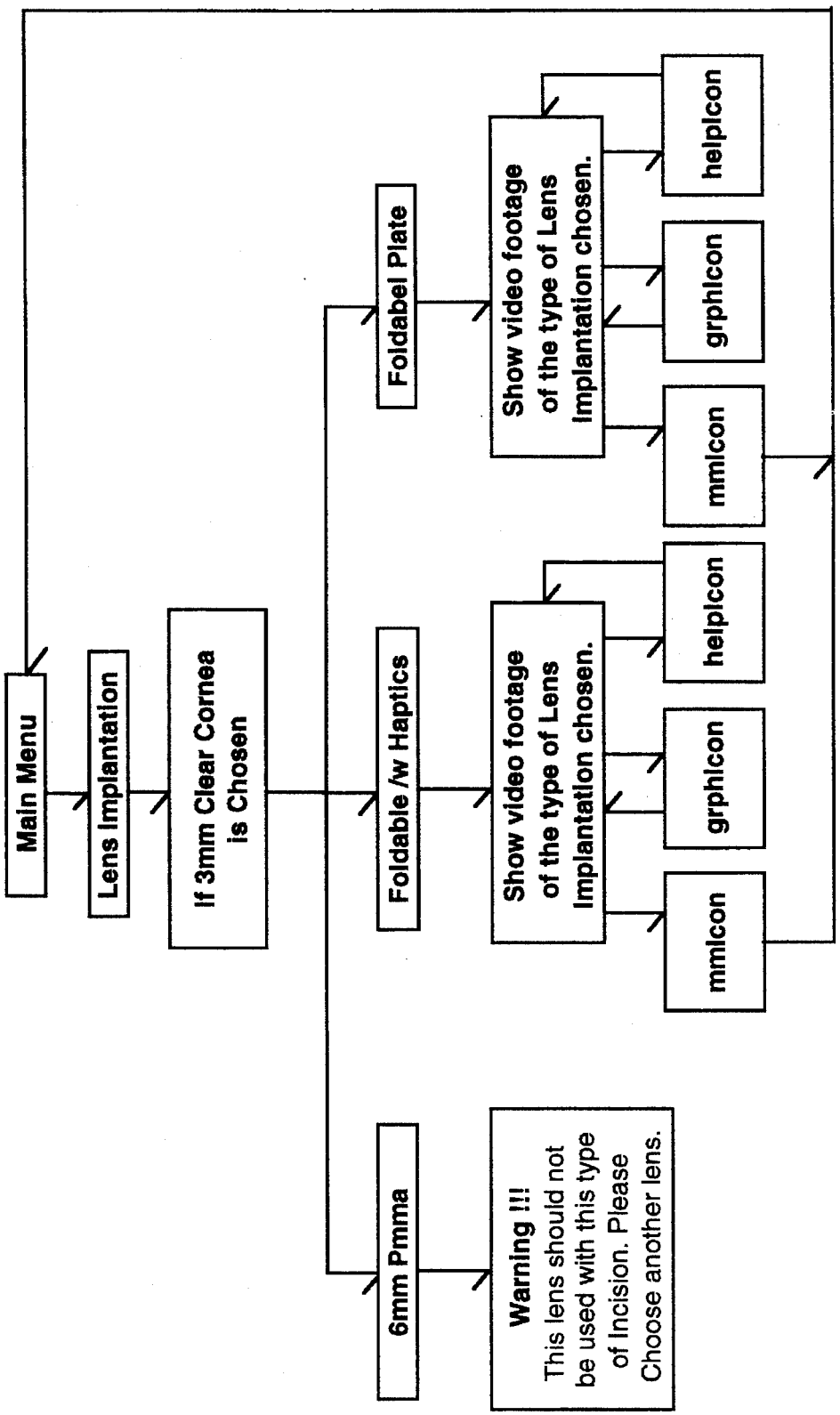
Figure 12:
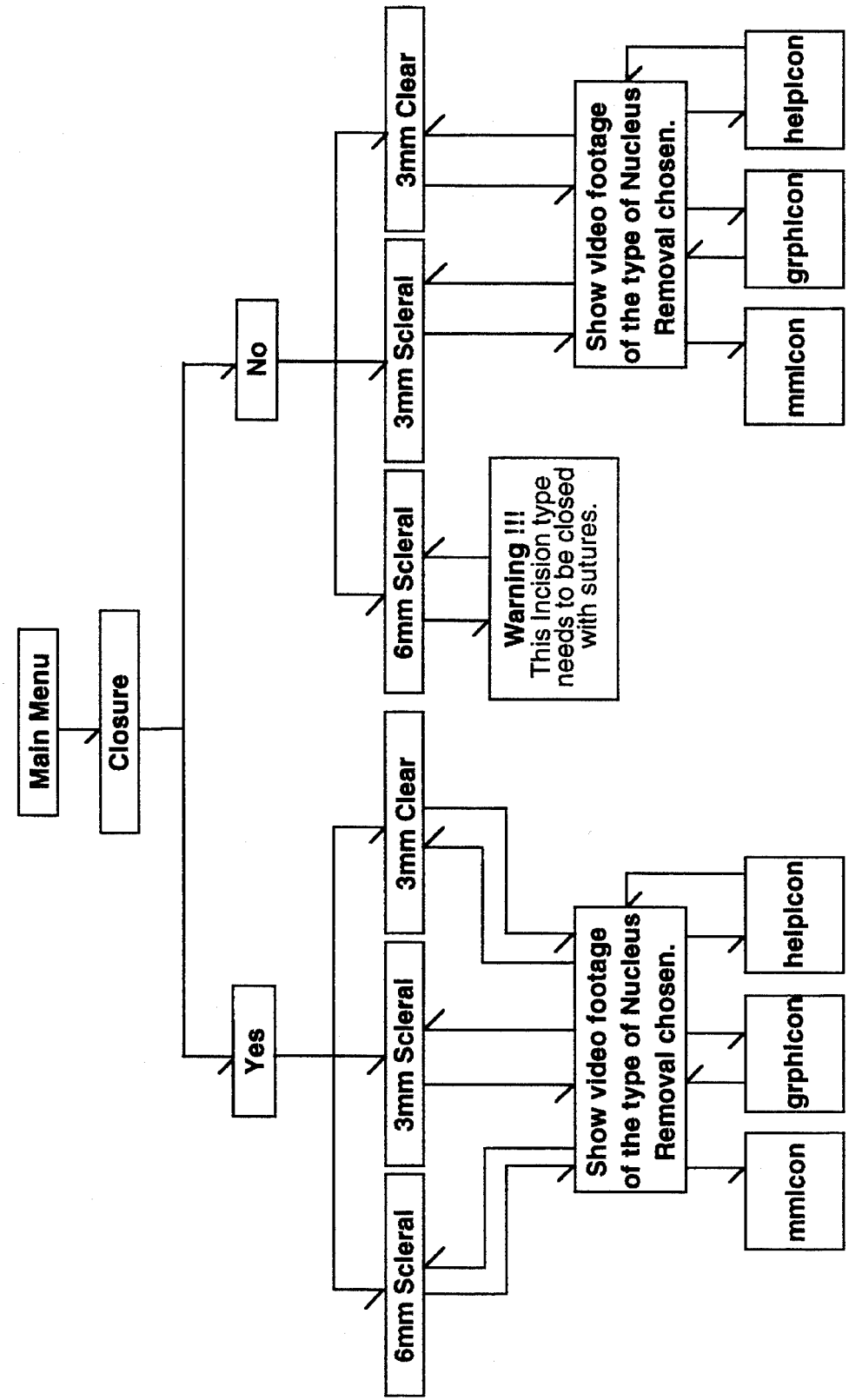

In addition to the above video, textual, and audio information, the user might also be provided with the option of viewing more information relating to the specified procedure by selecting a more information icon such as that shown in FIG. 3 as the "grphicon" area 56. This information might include graphical illustrations, additional video footage, further explanation of the procedure and possible complications which might arise during the procedure. The additional information is provided by the system when the user selects the "More Information" button on the screen, depicted in FIG. 5. For instance, shown in FIG. 5 is a flow chart for providing more detail of the incision step used in PHACO/IOL procedure.

The system may also be designed to test the user's knowledge of the specified procedure. For instance, as illustrated in the flow chart in FIG. 6, a user who incorrectly selects a can opener to perform a capsulotomy, is warned that he has selected an inappropriate instrument and is provided with instruction to select another instrument. Thus, the user would immediately be made to understand the error of his selection.

FIGS. 7 through 12 illustrate flow charts for the other possible users of the computer system 10, using the PHACO/IOL procedure as an example. Audio, graphical, and textual data would be provided in the same manner as described above with respect to the other steps in the procedure. The actual output of the remaining display screens and audio screens are dependent on the specific application and may be varied to suit particular preferences. Such modification and applications would be obvious to those skilled in the art.

A copy of the program code for the PHACO/IOL application of the system is appended hereto as Appendix A for a more detailed explanation of the specified system.

The system described herein could easily be translated into foreign languages by modifying the relevant textual and audio data bases. For instance, the audio and textual portions could be easily modified to provide Spanish or French explanations and prompts rather than English. Such modifications would only require modifications to the output data bases and would not require changes to the underlying code structure.

There are many possible modifications and changes which could be made to the system without straying from the applicants' present invention. Such modifications would be obvious to those skilled in the art and should not limit the scope of applicants' claimed invention.

We claim:

1. A method for providing a user with training in a surgical procedure utilizing a self-contained interactive computer system having a video display, a user interface device, and a memory storage device including a plurality of stored video footage relating to various steps in the surgical procedure, wherein a user selects from among a plurality of available actions relating to the various steps in the surgical procedure, said method comprising the steps of:

(a) providing a plurality of predetermined available actions relating to the surgical procedure on a first portion of the video display;

(b) detecting which of the plurality of such predetermined available actions was selected by the user with the user interface device;

(c) displaying on a second portion of the video display portion of the plurality of stored video footage in the memory storage device corresponding to the predetermined available action selected by the user; and (d) repeating steps (a) through (c) until either all scenarios relating to the surgical procedure are displayed on the video display, or an erroneous available action is selected by the user.

2. The method of claim 1 wherein the plurality of predetermined available actions provided in step (a) further include a plurality of erroneous surgical actions for testing the user's knowledge of the surgical procedure, and the method further comprising the steps of:

providing an error message on the first portion of the video display upon the selection of an erroneous surgical action by the user; and providing a return option on the first portion of the video display to enable the user to return to a previously depicted scenario.

3. The method of claim 2 wherein the surgical procedure is an ophthalmic surgical procedure.

4. The method of claim 3 wherein the ophthalmic surgical procedure is a PHACO/IOL procedure comprising the steps of incision, capsulotomy, nucleus removal, lens implantation and closure.

5. A method for training users in an ophthalmic surgery procedure with an interactive computer system having a plurality of stored video footage and stored data corresponding to various steps in the ophthalmic surgery procedure, a video display and a user interface device, said method comprising the steps of:

(a) providing an initial main menu on the video display prompting a user to select between a plurality of available procedures displayed on the main menu for treating an ophthalmic condition;

(b) detecting which of the plurality of available procedures is selected by the user with the user interface device;

(c) displaying a video image of an area of an eye on which the selected procedure is to be performed on a first portion of the video display and a plurality of actions corresponding to the selected procedure on a second portion of the video display;

(d) detecting which of the plurality of actions was selected by the user with the user interface device;

(e) updating the first portion of the video display with a portion of the plurality of stored video footage relating to the selected action;

(f) updating the second portion of the video display with a portion of the stored data corresponding to the selected action instructing a user as to the results of the selected action; and (g) repeating steps (c) through (f) for each subsequent step in the ophthalmic surgery procedure.

6. The method of claim 5 wherein the video display is further provided with a review button, a pause button and forward button display for rewinding, pausing and forwarding the video footage in the first portion of the video display.

7. A method for using an interactive computer system including an output video display, a user interface device and a memory storage system, including a video footage storage portion, a text storage portion and a program data storage portion, to provide training for a surgical procedure selected by a user, said method comprising the steps of:

(a) retrieving a program data from the memory storage system corresponding to the surgical procedure selected by the user;

(b) updating the output video display to display a main menu relating to a plurality of steps corresponding to the surgical procedure selected by the user;

(c) detecting which one of the plurality of surgical steps displayed on the main menu is selected by the sure with the user interface device;

(d) retrieving a video image and video footage from the video footage storage portion of the memory storage system, and program data from the program data storage portion of the memory storage system corresponding to the step selected from the main menu;

(e) displaying the video image on a first portion of the output video display corresponding to the video image retrieved from the video footage storage portion, and a plurality of selectable actions on a second portion of the output video display corresponding to the program data retrieved from the program data storage portion;

(f) detecting a selected one of the plurality of selectable actions displayed on the second portion of the output video display with the user interface device;

(g) displaying updated video footage on the first portion of the output video display corresponding to the selected one of the plurality of selectable actions whereby the output video display is updated with video footage stored in the video footage portion of the memory storage device corresponding to the selected one of the plurality of selectable actions;

(h) updating the second portion of the output video display with text data corresponding to the selected one of the plurality of selectable actions; and (i) repeating steps (f) through (h) until either all scenarios relating to the surgical procedure are completed or until an erroneous action for the scenario is selected.

8. The method of claim 7 wherein steps (g) and (h) are performed simultaneously on the output video display.

9. The method of claim 7 wherein video footage is displayed on the first portion of the output video display prior to displaying the video image of step (e).

10. The method of claim 7 wherein continuous video footage is displayed on the first portion of the video display instead of displaying the video image in step (e).

11. The method of claim 10 wherein steps (g) and (h) of claim 7 are performed simultaneously on the output video display.

* * * * *